United States Patent [19]
Takahashi et al.

[11] 4,158,625
[45] Jun. 19, 1979

[54] METHOD AND APPARATUS FOR DETECTING AND SCREENING FOREIGN MATTERS

[75] Inventors: Toshio Takahashi, Honjo; Ryosaku Tagaya, Isesaki, both of Japan

[73] Assignee: Eisai Co., Ltd., Tokyo, Japan

[21] Appl. No.: 820,308

[22] Filed: Jul. 29, 1977

[30] Foreign Application Priority Data

Aug. 20, 1976 [JP] Japan .................................. 51/98594

[51] Int. Cl.² .............................................. B07C 5/342
[52] U.S. Cl. ..................................... 209/524; 209/538; 250/223 B; 356/427
[58] Field of Search ............. 209/73, 74 R, 75, 111.5, 209/111.7 R, 111.7 T, 524, 576, 577, 588, 538; 250/223 B, 564, 565, 573, 574, 575, 576; 356/196, 197; 73/61 R

[56] References Cited

U.S. PATENT DOCUMENTS

| | | | |
|---|---|---|---|
| 3,528,544 | 9/1970 | Noguchi et al. | 209/73 |
| 3,765,533 | 10/1973 | Stephens et al. | 209/73 |
| 4,050,824 | 9/1977 | Woodrow et al. | 356/197 |
| 4,058,737 | 11/1977 | Takahashi et al. | 356/197 X |
| 4,087,184 | 5/1978 | Knapp et al. | 250/223 B X |
| 4,095,904 | 6/1978 | Klein et al. | 356/197 |

FOREIGN PATENT DOCUMENTS

1154025  6/1969  United Kingdom ..................... 356/197

Primary Examiner—Joseph J. Rolla
Attorney, Agent, or Firm—Blanchard, Flynn, Thiel, Boutell & Tanis

[57] ABSTRACT

The characteristics of detecting and screening foreign matters that might be present in samples (e.g., ampoules containing a medical fluid) are improved by subjecting samples to more than two foreign matter detectors consecutively, applying the output signals from the detectors to paired comparators in which the comparing reference voltage is set to a high level and a low level, with the detectors being connected to the signal delay circuits that adjust with one another the output time of signals from the comparators, applying all the output signals from the comparators of the high level to an AND circuit and applying all the output signals from the comparators of low level to an OR circuit and further applying the output signals from the AND circuit and the output signals from the OR circuit to another OR circuit.

12 Claims, 2 Drawing Figures

METHOD AND APPARATUS FOR DETECTING AND SCREENING FOREIGN MATTERS

BACKGROUND OF THE INVENTION

The present invention relates to a method and apparatus for detecting and screening foreign matters that might be present in medical fluids, toiletry fluids, chemical fluids, drinks, etc. filled in transparent or translucent ampoules, vials, or bottles.

The present invention will be illustrated by an example of an inspection operation to determine the presence or absence of small particles in ampoules containing a medical fluid.

For a detecting and screening machine that detects small particulate foreign matters that might be present in a medical fluid contained in ampoules and screens the ampoules automatically in place of visual inspection, it is required that only those ampoules which contain particles larger than the standard (hereinafter called large foreign matters) should be screened and rejected and other ampoules which contain particles smaller than the standard (hereinafter called small foreign matters) should be accepted.

Usually, defective ampoules containing large foreign matters account for only a small portion of the total number of ampoules, while acceptable ampoules containing small foreign matters that will not affect the quality account for a large portion in the entire ampoules. This in enhanced more as small foreign matters decrease in size. Consequently, if the detecting sensitivity is increased in an attempt to catch large foreign matters completely, small foreign matters are also caught. This increases the rejected fraction and decreases the productivity.

If, conversely, the detecting sensitivity is lowered in an attempt to decrease the rejected fraction, large foreign matters tend to be overlooked and the quality of the entire lot will be severely degraded.

In an actual example in which the detecting sensitivity was set at a high level, the detection was repeated twice, and any ampoules that reacted to either detection were rejected, nearly all (99.7%) defective ampoules were rejected; at the same time, however, many acceptable ampoules were also rejected and the rejected fraction increased more than 4%. In another example in which the detecting sensitivity was set at a low level, the detection was repeated twice, and any ampoules that reacted to either detection were rejected, the rejected fraction was less than 1% but the ratio of defective ampoules rejected was about 90%.

The method in which the samples are detected once each with the sensitivity set at a high level and at a low level provided an intermediate ratio, which as not yet satisfactory.

In order to satisfy these two contradictory conditions, it is necessary to improve the detecting and screening characteristics (the relationship between the particle size and the reject ratio) so that foreign matters larger than a certain standard can be caught completely.

The detection of small particles in an ampoule is accomplished by turning the ampoule and then bringing it quickly to a standstill, causing the small particles in the fluid to be suspended and swirled. Thus the same particle in an ampoule differs in its position, movement, and posture with respect to the detector, each time when detection is accomplished, and accordingly the output signals to be generated in the detector corresponding to the same particle also varies to some extent. This suggests that large foreign particles might be overlooked if only one detection is provided. For positive detection of small particles, it is indispensable to repeat more than twice the detection of the same ampoule.

On the other hand, small foreign matters will generate signals exceeding the screening standard when the detection is repeated over and over again. For instance, assume an ampoule containing a small particle which will be judged to be unacceptable at a rate of once in one hundred detections. Incidentally, the detection rate of this small particle is 1%. In a given lot there are a large number of ampoules that contain small particles of about 1% detection rate. Therefore, the more the number of detections is increased, the higher will be the defective fraction.

BRIEF SUMMARY OF THE INVENTION

It is an object of this invention to provide a very effective means to improve the characteristics for detecting foreign matters.

To this end the detection and screening are accomplished in this invention as mentioned below. Samples are subjected to a plurality of foreign matter detectors consecutively; the output signals from the detectors are applied to paired comparators in which the comparing reference voltage is set at a high level and at a low level; the timing for the output signals from these comparators are adjusted with each other by delay circuits; all the output signals from the comparators of high level are applied to an AND circuit so as to obtain outputs that will decrease the rate of judging small foreign matters to be unacceptable; all the output signals from the comparators of low level are applied to an OR circuit so as to obtain outputs that will increase the rate of judging large foreign matters to be unacceptable; the output signals from the AND circuit and the output signals from the OR circuit are applied to another OR circuit; and the output signals from the last OR circuit are utilized for screening. In this way the object of the invention is accomplished very effectively.

It is another object of this invention to provide an apparatus to realize the above-metioned method for detecting and screening foreign matters.

It is further object of this invention to provide an apparatus that permits one to set the detecting characteristics at will by varing the comparing reference value.

Other features and advantages of the invention will be apparent from the following description taken in connection with the accompanying drawings.

DETAILED DESCRIPTION

Figure 1:
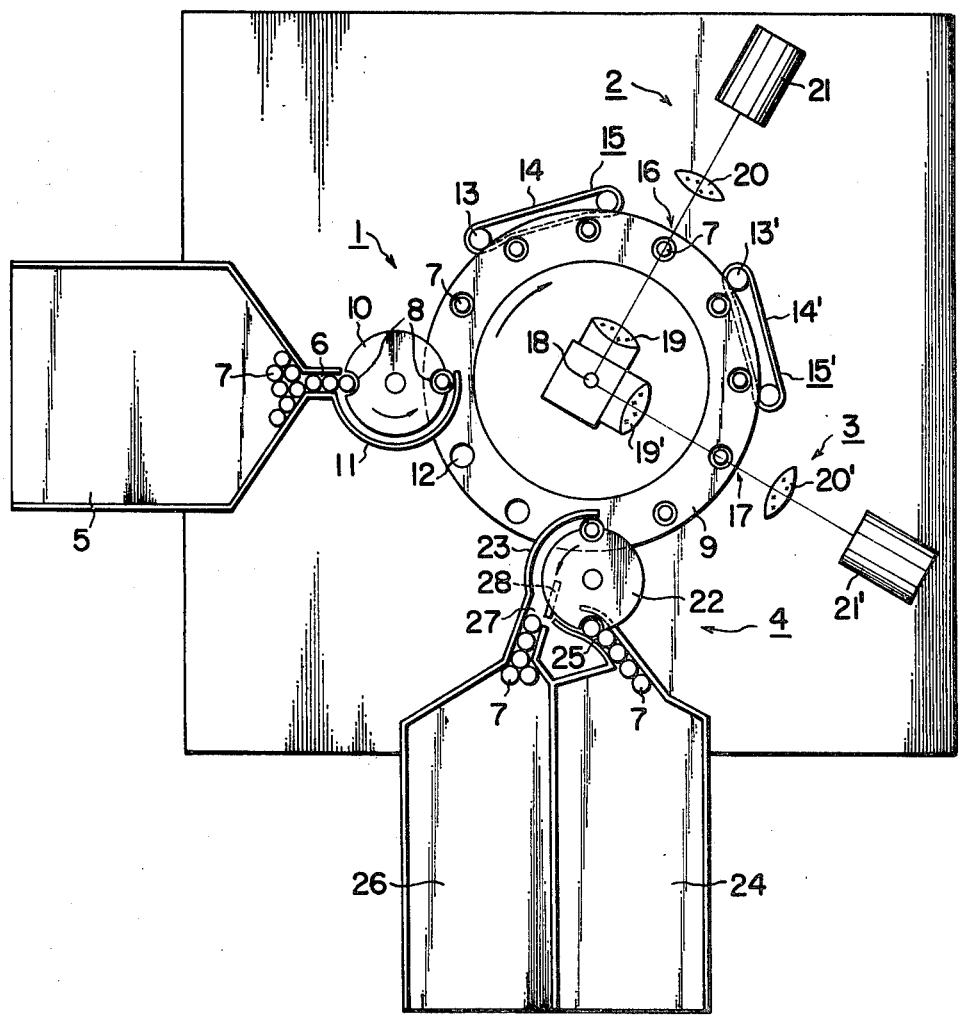
FIG. 1 is a plan view showing one example of the detecting and screening apparatus according to the present invention.

To illustrate an example according to the invention, an automatic ampoule fluid detecting machine will be described.

This machine consists of four major units: the ampoule supply and conveyor unit (1), the first detector unit (2), the second detector unit (3), and the ampoule selector and collector unit (4). The ampoule supply hopper (5) included in the said supply and conveyor unit (1) has a bottom plate which is inclined toward the outlet (6), so that the ampoules (7) stored in the hopper are fed to the outlet (6) by gravity or by gravity and a net conveyor (not shown) in combination. At the outlet (6) of the hopper (5) is provided the supply star wheel (10) having the engaging notches (8), which rotates synchronously with the turn table (9). A semicircular portion of the star wheel (10) is surrounded by the guide (11) extending from the outlet (6). On the top of the turn table (9) are provided the ampoule carriers (12) at regular intervals, and the turn table (9) turns intermittently at the same angle as the interval separating adjacent carriers (12). As the ampoule (7) is fed to the ampoule carrier (12) on the turn table (9) via the engaging notch (8) of the supply star wheel (10), the turn table (9) transfers the ampoule (7) by intermittent movement. During this intermittent movement, the ampoule (7) on the ampoule carrier (12) is pressed from above and held firmly by the spring-supported upper cap.

Along the periphery of the turn table (9) and immediately before the first and second detector units (2) and (3) are provided the rotary agitators (15) and (15') consisting of the drive pulley (13) and the belt (14). The ampoule (7) which has been driven at a high speed by the rotary agitators (15) and (15') are brought to a standstill at the detecting positions (16) and (17), respectively, for detection.

The said first and second detector units (2) and (3) consist of the projector lamp (18), the condenser lenses (19) and (19'), the image forming lenses (20) and (20'), the detectors (21) and (21'), and the arithmetic circuit (29) to be described into detail later. On the periphery of the star wheel (22) of the ampoule selector and collector unit (4) is provided the guide (23), along which are provided the inlet (25) for the acceptance hopper (24) and the inlet (27) for the reject hopper (26). Immediately before these inlets (25) and (27) is provided the selector lever (28) which is actuated according to the result of arithmetic operations.

Figure 2:
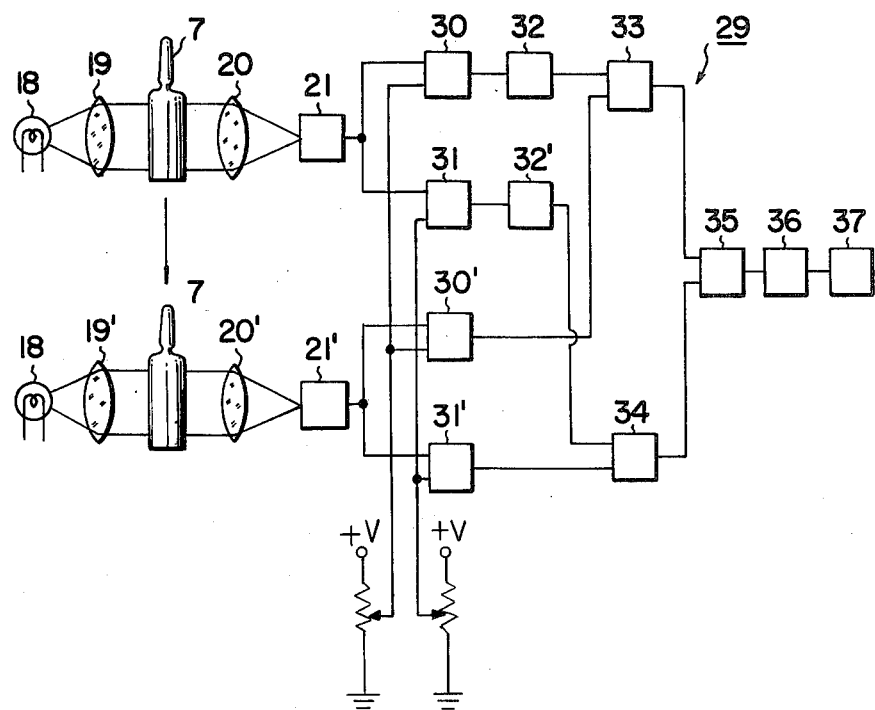
FIG. 2 is a block diagram of the detector unit.

The said arithmetic circuit (29) is described referring to FIG. 2. The first and second detectors (21) and (21') consist of 1024-bit self-scanning MOS diode arrays having 1024 pieces of light receiving units, $18\mu \times 26\mu$ in size. Small particles that might be present in the fluid will mask partially the beam of light from the projector lamp (18), causing some of the 1024 light receiving units corresponding to the shadows of the particles to generate output signals. Other examples of the detectors (21) and (21') include BBD, CCD, phototransistor, photomultiplier tube, vidicon, optical fiber rotary scanning light receiver, and the like.

In this example the detection is accomplished by the use of transmitted light, but the detection by the use of reflected light may be employed in other examples.

To the detectors (21) and (21') are connected the paired comparators (30) (31) and (30') (31'), respectively. The comparators (30) and (31') are designed for high sensitivity, with the comparing reference voltage set to a high level $V_H$; and the comparators (31) and (31') are designed for low sensitivity, with the comparing reference voltage set to a low level $V_L$.

In this invention "high level" means a state in which the comparing reference voltage of the comparator is decreased to such an extent that small and large foreign matters can be caught; and "low level" means a state in which the comparing reference voltage of the comparator is increased to such an extent that only large foreign matters can be caught.

These levels $V_H$ and $V_L$ can be set to any value by means of variable resistors inserted in circuit with the comparators (30) (31) and (30') (31').

One pair of the comparators (30) and (31) are connected consecutively to the signal delay circuits (32) and (32') consisting of shift registers, so that signals from the comparators are delayed for a period of t sec. which is equivalent to the transfer time from the first detection to the second detection. The signal delay circuit (32) and the comparator (30') of the other pair are connected to the AND circuit (33); and the other signal delay circuit (32') and the comparator (31') of the other pair are connected to the OR circuit (34).

The AND circuit (33) and the OR circuit (34) are further connected to the OR circuit (35), which is connected through the amplifier (36) to the solenoid (37) for mechanical actuation of the selector lever (28).

The function of the apparatus according to the invention is described below.

The sample ampoules (7) are fed from the ampoule supply hopper (5) to the ampoule carriers (12) on the turn table (9) through the supply star wheel (10). The ampoule is rotated by the rotary agitator (15) so that small particles in the fluid are suspended, and then transferred to the first detector unit (2).

In the first detector unit (2), the light from the projector lamp (18) is made parallel rays by the condenser lens (19) and the parallel rays irradiate the ampoule (7). The light which has passed through the medical fluid is collected on the detector (21) by the image forming lens (20), so that an image of the medical fluid is formed. The output signals from this detector (21) are applied to the comparators (30) and (31) and, after digital conversion by the comparators (30) and (31), are stored in the delay circuits (32) and (32') for a period of t sec.

The same ampoule (7) is rotated again by the rotary agitator (15') and then transferred to the second detector unit (3) in which the same detection as above is carried out. Thus the compensators (30') and (31') generate output signals.

The output signals from the comparators (30) and (30') of high level in the first and second detector units (2) and (3) are applied to the AND circuit (33). The output appearing in the AND circuit (33) is such that the rate of judging small foreign matters smaller than the screening standard to be defective is decreased more. On the other hand, the output signals from the comparators (31) and (31') of low level in the first and second detector units (2) and (3) are applied to the OR circuit (34). The output appearing in the OR circuit (34) is such that the rate of judging large foreign matters larger than the screening standard to be defective is increased more. The output signals from the AND circuit (33) and the output signals from the OR circuit (34) are applied further to another OR circuit (35). This provides the output signal that accomplishes the object of this invention very effectively. This output signal is amplified by the amplifier (36) to energize the solenoid (37) which actuates the selector lever (28) when the ampoule (7) reaches the ampoule selector and collector unit (4). The selector lever (28) introduces the ampoule (7) to the acceptance inlet (25) or the reject inlet (27). Conforming ampoules are collected in the acceptance hopper (24) and defective ampoules are collected in the reject hopper (26).

The ampoule detecting machines of this invention and conventional method gave the following comparative data for 100,000 ampoules consisting of 1,000 ampoules containing large foreign matters larger than the screening standard and 99,000 ampoules containing small foreign matters smaller than the screening standard.

| Detecting system | Number of ampoules judged to be defective (pc.) | | | Rate of ampoules judged to be defective (%) | | |
|---|---|---|---|---|---|---|
| | Larger than standard | (Over- looked) | Smaller than standard | Over- all | Larger than standard | Smaller than standard |
| A + A | 997 | (3) | 4,106 | 5.1 | 99.7 | 4.1 |
| A + B | 986 | (14) | 2,075 | 3.6 | 98.6 | 2.8 |
| B + B | 902 | (98) | 137 | 1.0 | 90.2 | 0.14 |
| This invention | 996 | (4) | 152 | 1.1 | 99.6 | 0.15 |

Remarks:
"A" and "B" indicate the high level and low level, respectively, of the comparing reference set voltage in the comparator.

This result indicates that the detecting system according to the invention catches 99.6% of defective ampoules containing large foreign matters larger than the screening standard and catches only 0.15% of acceptable ampoules containing small foreign matters smaller than the screening standard.

Although the above-mentioned example employs two sets of the detector units (2) and (3), more sets of the detector units can be employed without departing from the scope of the invention. In the case of three sets, for instance, the object of the invention is accomplished in the following manner. Three detectors are connected respectively to three sets of paired comparators in which the comparing reference voltage is set to high level and low level. All of the comparators or at least the first and second sets of comparators are connected to respective delay circuits so that output times of the signals is synchronized. Output signals from the three comparators of high level are applied to an AND circuit, and output signals from the three comparators of low level are applied to an OR circuit. The output signals from the AND circuit and the OR circuit are applied further to another OR circuit.

In such a case, it is possible to set the comparing reference voltage to any value by changing the respective levels of the comparators of high level and/or the comparator of low level. By varying the comparing reference voltage the detecting characteristics can be set as desired.

In the above example the detection is accomplished twice at different positions and different times, but the detection may be accomplished at the same position and the same time or different times using beams of light in different directions.

Although the invention has been described in its preferred form, it is understood that the invention is not limited to the specific embodiments thereof and different embodiments of the invention may be made without departing from the spirit and scope thereof.

What we claim is:

1. A method for detecting and screening foreign matter, which comprises the steps of: generating a plurality of output signals from a plurality of detectors which signals are indicative of the presence or absence of foreign matter in a single sample; applying said detector output signals respectively to different pairs of comparators, simultaneously applying comparing reference voltages to the comparators of each pair so that one comparator of each pair is a high sensitivity comparator and the other comparator of each pair is a low sensitivity comparator, and generating comparator output signals in response to said detector output signals; simultaneously applying the output signals from all of said high sensitivity comparators to an AND circuit to generate an output signal from said AND circuit and simultaneously applying the output signals from all of said low sensitivity comparators to a first OR circuit to generate an output signal from said first OR circuit; simultaneously applying said output signal from said AND circuit and said output signal from said first OR circuit to a second OR circuit to generate an output signal from said second OR circuit; and utilizing said output signal from said second OR circuit to accept or reject said sample.

2. A method according to claim 1 in which the respective output signals from said detectors are spaced-apart in time and including the step of delaying the signals from all of the detectors, except the last one, so that said signals from a single sample are applied to said AND circuit and said first OR circuit simultaneously.

3. A method according to claim 1 including varying the comparing reference voltages applied to said comparators to adjust the sensitivities thereof.

4. A method for inspecting the contents of a container filled with liquid and detecting the presence of foreign particles therein, which comprises the steps of: generating a plurality of separate detector output signals from a plurality of detectors which detector output signals are generated under different conditions and are indicative of the presence of foreign particles in a container's contents; applying said detector output signals respectively to different pairs of comparators wherein each pair of comparators consists of a high sensitivity comparator and a low sensitivity comparator, generating from the respective high sensitivity comparators first comparator output signals indicative of the presence of both small size particles and large size particles in said container's contents, and generating from the respective low sensitivity comparators second comparator output signals inidicative of the presence of only large size particles in said container's contents; simultaneously applying said first comparator output signals to an AND circuit and generating an output signal from said AND circuit; simultaneously applying said second comparator output signals to a first OR circuit and generating an output signal from said first OR circuit; simultaneously applying the output signals of said AND circuit and said first OR circuit to a second OR circuit and generating an output signal from said second OR circuit; and utilizing said output signal from said second OR circuit to accept or reject said container.

5. A method according to claim 4 in which said separate detector output signals are spaced-apart in time and including the steps of delaying said first comparator output signals except the last one thereof and delaying said second comparator output signals except the last one thereof so that all of said first comparator output signals are simultaneously applied to said AND circuit and all of said second comparator signals are simultaneously applied to said first OR circuit.

6. A method according to claim 4 in which the sensitivities of said high sensitivity comparators and said low sensitivity comparators are adjusted by varying comparing reference voltages which are applied to said comparators simultaneously with said detector output signals.

7. An apparatus for detecting and screening foreign matter, which comprises: means to supply and transfer samples to be inspected along a path of travel; means to rotate the samples on said supply and transfer means; at least two detector units, each of said detector units comprising a light source, a condenser lens, an image-forming lens and a photodetector arranged in series with said condenser lens and said image-forming lens being arranged on opposite sides of the path of travel of samples on said supply and transfer means so that said photodetector provides an output signal indicating the presence of foreign matter in a sample, each of said detector units including a high sensitivity comparator and a low sensitivity comparator connected for receiving an output signal from said photodetector and adapted for generating respective comparator output signals in response to said photodetector output signal; an AND circuit connected to said high sensitivity comparators of said detector units for providing an output signal in response to said output signals of said high sensitivity comparators; a first OR circuit connected to said low sensitivity comparators of said detector units for providing an output signal in response to said output signals of said low sensitivity comparators; a second OR circuit connected to said AND circuit and said first OR circuit for providing an output signal in response to said output signal of said AND circuit and said output signal of said first OR circuit; and means operable by said output signal of said second OR circuit for accepting or rejecting a sample.

8. An apparatus according to claim 7 including time delay means in circuit in each of said detector units, except the detector unit that detects the sample last, so that the signals from one sample are simultaneously supplied from all of said detector units to said AND circuit and said first OR circuit.

9. An apparatus according to claim 7 including variable reference voltage means connected to said comparators for varying the sensitivities thereof.

10. An apparatus for inspecting the contents of containers filled with liquid and detecting the presence of foreign particles therein, which comprises: conveyor means for translating containers through a plurality of inspection stations; scanning means for transmitting radiant energy through the containers at each inspection station; a detector at each inspection station for producing an output signal in response to the radiant energy transmitted through the contents of each container at each inspection station; a high sensitivity comparator and a low sensitivity comparator connected to each detector, said high sensitivity comparator and said low sensitivity comparator generating respective output signals in response to the output signal from their associated detector and which are respectively indicative of (1) the presence of both large size particles and small size particles in the container contents and (2) the presence of only large size particles in the container contents; an AND circuit connected to said high sensitivity comparators for providing an output signal in response to the output signals of said high sensitivity comparators; a first OR circuit connected to said low sensitivity comparators for providing an output signal in response to the output signals of said low sensitivity comparators; a second OR circuit connected to said AND circuit and said first OR circuit for providing an output signal in response to said output signal of said AND circuit and said output signal of said first OR circuit; and means operable by said output signal of said second OR circuit for accepting or rejecting a container.

11. An apparatus according to claim 10 including time delay means for delaying the signals from each detector, except the detector at the last inspection station, so that the signals from one sample are simultaneously applied to said AND circuit and said first OR circuit.

12. An apparatus according to claim 10 including variable reference voltage means connected to said comparators for varying the sensitivities thereof.

* * * * *